United States Patent [19]

Watanabe

[11] Patent Number: 5,050,199
[45] Date of Patent: Sep. 17, 1991

[54] RADIOGRAPHIC APPARATUS

[75] Inventor: Naoto Watanabe, Nishinasunomachi, Japan

[73] Assignee: Kabushiki Kaisha Toshiba, Kawasaki, Japan

[21] Appl. No.: 538,910

[22] Filed: Jun. 15, 1990

[30] Foreign Application Priority Data

Jun. 16, 1989 [JP] Japan .................................. 1-153868

[51] Int. Cl.$^5$ ............................................. G21K 5/10
[52] U.S. Cl. ...................................... 378/146; 378/147
[58] Field of Search ................................ 378/146, 147

[56] References Cited

U.S. PATENT DOCUMENTS

| | | | |
|---|---|---|---|
| 4,096,391 | 6/1978 | Barnes | 378/146 |
| 4,097,748 | 6/1978 | Monvoisin | 378/146 |
| 4,355,409 | 10/1982 | Amplatz | 378/146 |
| 4,841,555 | 6/1989 | Doi et al. | 378/99 |

OTHER PUBLICATIONS

Medical Physics, vol. 6, No. 3, May/Jun. 1979, New York (US); pp. 197–204, Barnes and Brezovich: "The Design and Performance of a Scanning Multiple Slit Assembly,", 1.1.–pp. 200, 1.12.

*Primary Examiner*—Craig E. Church
*Attorney, Agent, or Firm*—Oblon, Spivak, McClelland, Maier & Neustadt

[57] ABSTRACT

A radiographic apparatus includes an X-ray generator for radiating X-rays, two slit members sequentially arranged to oppose the X-ray generator, a subject being arranged between the slit members, and each of the slit members having at least one linear slit for narrowing down X-rays to obtain a slit-like X-ray beam, a slit member moving unit for moving the slit members in such a manner that an X-ray tube focal point and the slits of the slit members are always aligned with each other, and a cassette film for two-dimensionally recording a slit-like X-ray beam obtained by causing X-rays to pass through the object and the linear slits of the slit members.

18 Claims, 8 Drawing Sheets

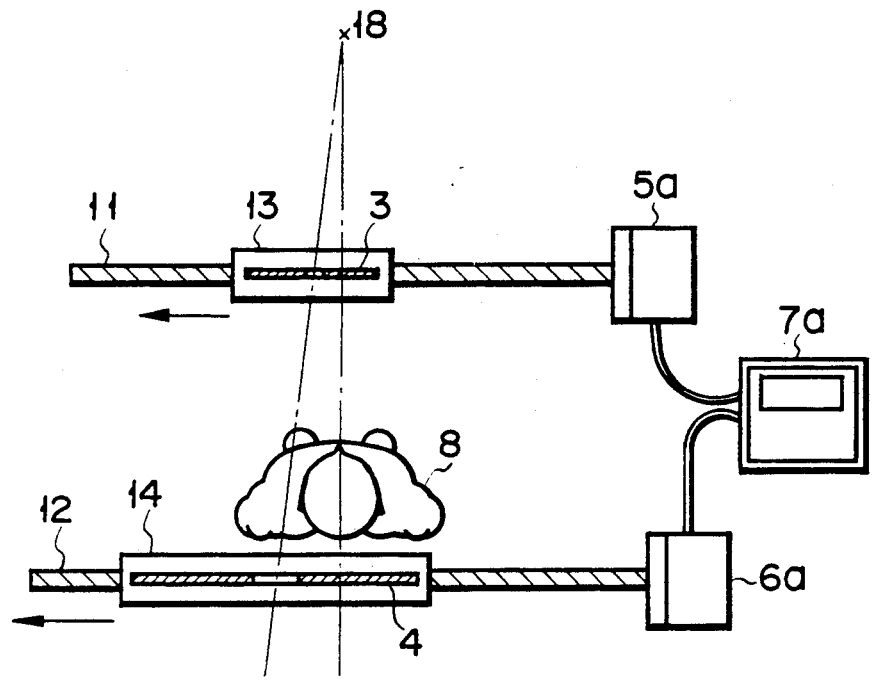
F I G. 3
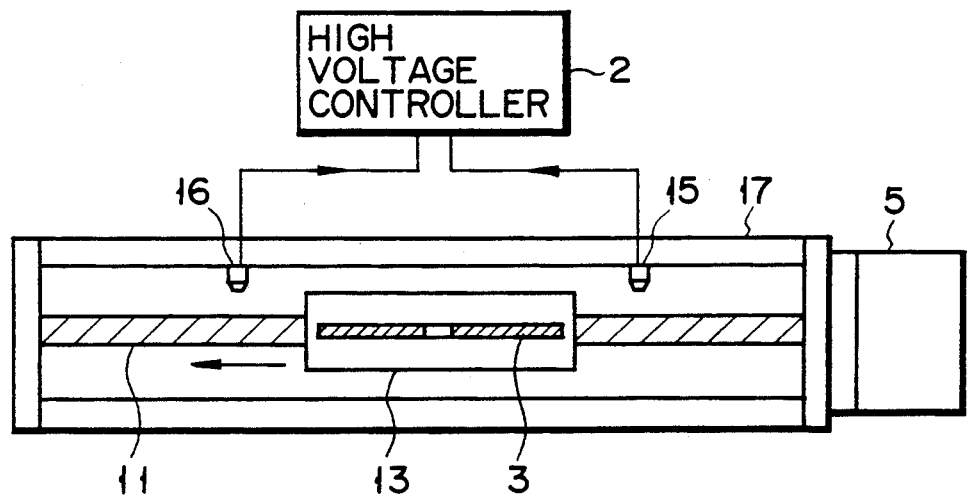
F I G. 4

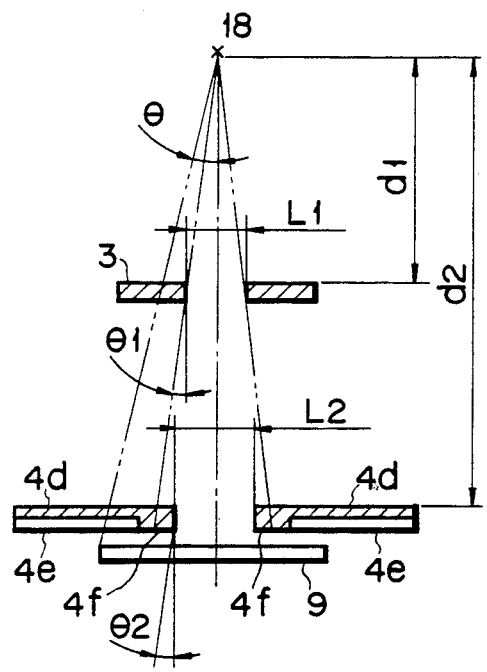 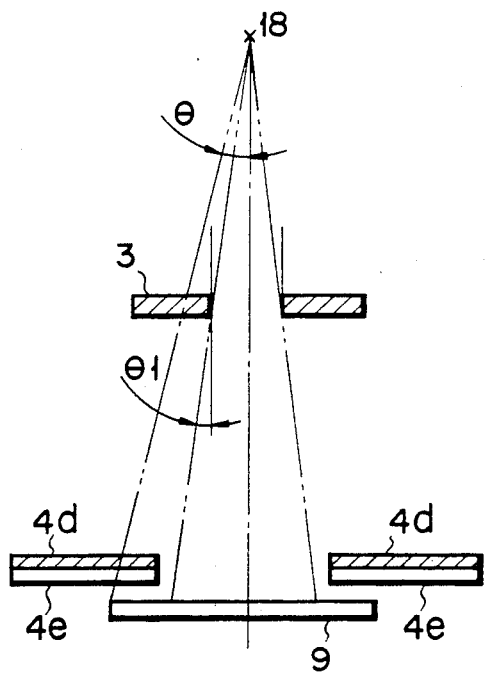
F I G. 7A  F I G. 7B
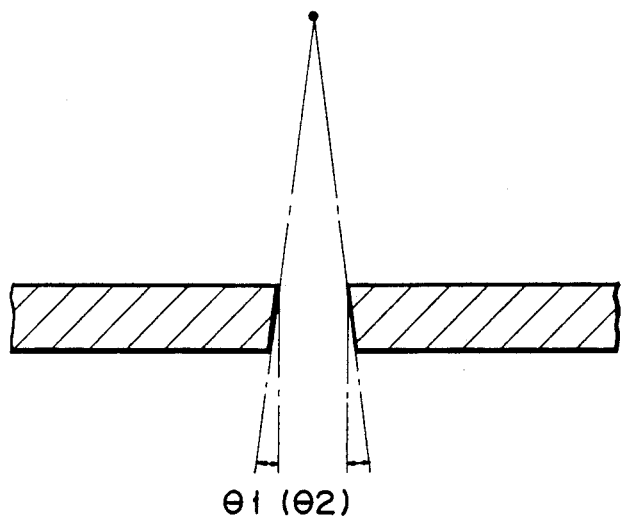
F I G. 8

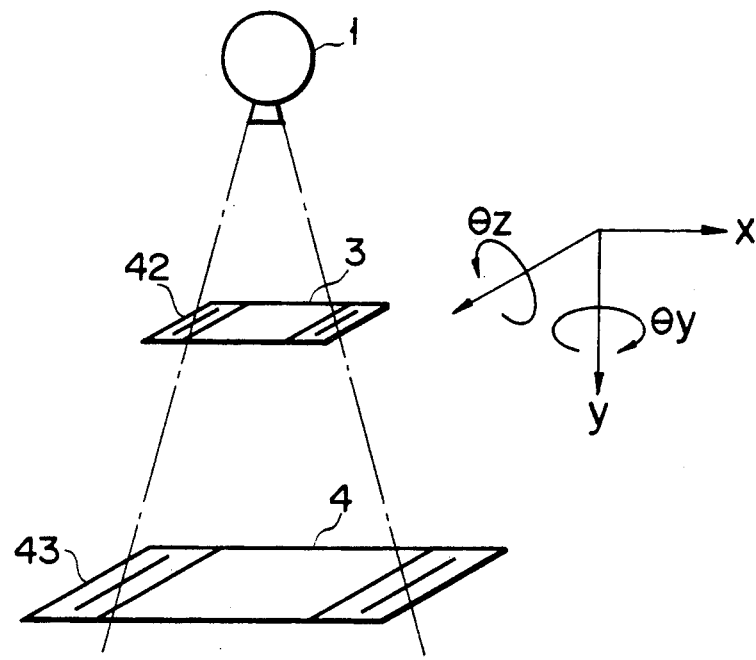
F I G. 12
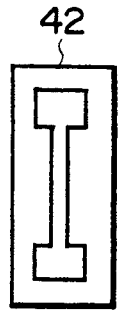
F I G. 13A
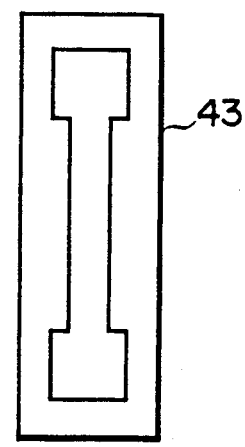
F I G. 13B $\theta y = \theta$
$\theta y \rightarrow 0$ $x = \dfrac{b-a}{2}$
$x \rightarrow 0$ $c \rightarrow 0$

RADIOGRAPHIC APPARATUS

BACKGROUND OF THE INVENTION

1. Field of the Invention

The present invention relates to an X-ray diagnostic apparatus or a radiographic apparatus having a function for removing scattered X-rays.

2. Description of the Related Art

When radiography is to be performed in a radiographic apparatus, X-rays are radiated from an X-ray source onto an object to be examined at a relatively large dose, and the X-rays transmitted through the object are recorded on an X-ray recording medium (an X-ray film cassette) arranged within the X-ray radiation range. In this radiographing method, however, the X-rays are scattered by the object, and a radiographic image includes a large amount of scattered X-rays from the object, resulting in degradation of the image quality of the radiographic image.

For this reason, the following radiographic apparatus has been developed. In this apparatus, in order to obtain one radiographic image, X-rays are radiated on a subject while they are formed into a slit-like beam by a slit, or X-rays which are transmitted through the subject upon radiation are formed into a slit-like beam by a slit, and the slit is moved.

According to another system, X-rays are formed into a slit-like beam, and are radiated along a subject. X-rays which are transmitted through the subject are converted into an electrical signal by a line sensor. While slit-like radiographic data is obtained in this manner, the slit-like X-ray beam and the sensor position are synchronized with each other, thus obtaining one radiographic image.

In a radiographing operation using one slit member as described above, scattered X-rays from a subject cannot be effectively removed. For example, when X-rays are radiated on a subject after they are narrowed down by a slit, since the X-rays are scattered in the subject, the X-rays transmitted through the subject have an inverted U-shaped distribution and spread in a wide range. When X-rays are narrowed down by a slit after they are radiated on the subject, the X-rays transmitted through the slit have a narrower distribution than the former case. However, since scattered X-rays from the subject pass through the slit, the amount of scattered X-rays becomes large as in the former case. In addition, since X-rays are radiated on the entire subject in a radiographing time, the dose of X-ray radiation on the subject is increased.

Furthermore, since a line sensor is constituted by a CCD sensor having a fluorescent material in its light-receiving surface, it is inferior to a film in terms of technical limitations on the sensor length, pixel variations, dynamic range, and the like. In addition, the conventional radiographic apparatus is complicated in electronic arrangement. Moreover, the resolution is degraded upon movement of a subject due to limitations on the operation speed of an electronic circuit.

SUMMARY OF THE INVENTION

It is an object of the present invention to provide a radiographic apparatus which can minimize the influences of scattered X-rays, can realize a simple arrangement, and can prevent degradation of resolution without causing overlapping or omission of an image.

According to the present invention, there is provided a radiographic apparatus comprising two slit members arranged on face and back sides of a subject and having linear slits, a driving unit for moving the subject and the two slit members relative to each other, a controller for controlling the driving unit, and a recording member for two-dimensionally recording X-rays which are radiated from an X-ray source onto the subject and pass through the subject and the slits of the two slit members.

According to the present invention, by using the two-dimensional recording member as an X-ray detector, a conventional radiographic apparatus and image processor can be used without modifications, thus obtaining a simple structure. In addition, since the two slit members are arranged, scattered X-rays can be effectively removed, and an image faithfully reflecting the absorption coefficient of each human organ can be obtained, thereby greatly improving detection ability of a morbid portion.

By using a slit member having a plurality of slits, the moving distance of the slit member can be reduced. This allows a smaller radiographic apparatus, a shorter radiographing time, a shorter radiographing time interval associated with the allowable load of an X-ray source, and a longer service life of the X-ray source.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 3 is a view showing an arrangement of a slit device in detail;

FIG. 4 is a view showing a slit unit of the slit device in FIG. 3;

FIGS. 7A and 7B are sectional views of slit members having inclined wall surfaces;

FIG. 8 is a partially enlarged sectional view of the slit member in FIG. 7A;

FIG. 12 is a view for explaining a method of detecting a positional error by using a photopattern; and FIGS. 13A to 13F are views respectively showing photopatterns.

DETAILED DESCRIPTION OF THE PREFERRED EMBODIMENTS

Figure 1:
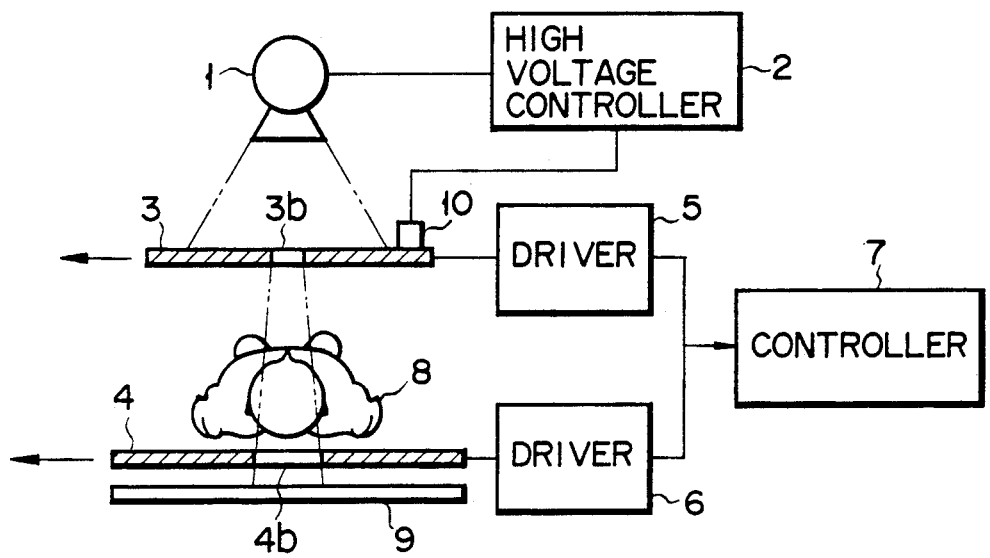
FIG. 1 is a schematic view showing an arrangement of a radiographic apparatus according to an embodiment of the present invention.
Figure 2:
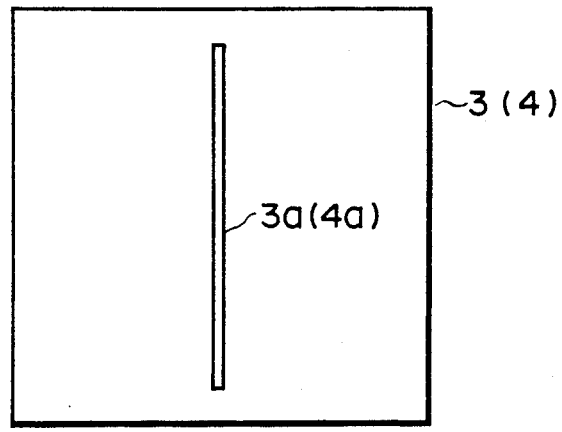
FIG. 2 is a plan view of a slit member.

In a radiographic apparatus shown in FIG. 1, an X-ray tube 1 is energized by a control signal from a high voltage controller 2 so as to radiate X-rays onto a subject 8. A slit member 3 is arranged to oppose the X-ray tube 1. A slit member 4 is arranged to oppose the slit member 3. The slit members 3 and 4 are respectively constituted by X-ray shielding plates each having a linear slit 3b (4b) formed in its middle portion, as shown in FIG. 2, and are designed to be movable in a direction indicated by arrows. In this case, the slit members 3 and 4 are movably arranged such that the opening centers of the slits 3b and 4b are positioned on a straight line extending to the tube focal point of the X-ray tube 1. The subject 8 is arranged in a space between the slits 3 and 4. A two-dimensional sheet (film cassette) is arranged below the lower slit member 4.

The slit members 3 and 4 are respectively coupled to drivers 5 and 6 so as to be synchronously moved in the direction indicated by the arrows. The drivers 5 and 6 are coupled to a driver controller 7 and are controlled by control signals from the controller 7.

A slit position sensor 10 is mounted on an end portion of the upper slit member 3 so as to send a position signal corresponding to the moving position of the slit member 3 to the high voltage controller 2. With the arrangement, an X-ray radiation timing is synchronized with the movement of the slit member 3.

The arrangement shown in FIG. 1 will be described in more detail below with reference to FIG. 3.

The slit members 3 and 4 are respectively coupled to screw shafts 11 and 12 coupled to step motors 5a and 6a. The step motors 5a and 6a are coupled to a biaxial synchronous driving motor controller 7a. The controller 7a controls the step motors 5a and 6a so as to move the slit members 3 and 4 in such a manner that the straight line connecting the opening centers of the slits 3b and 4b of the slit members 3 and 4 always passes through a tube focal point 18. More specifically, the slit members 3 and 4 are respectively mounted on slit mounting bases 13 and 14 threadably engaged with the screw shafts 11 and 12. When the screw shafts 11 and 12 are respectively rotated by the step motors 5a and 6a, the slit members 3 and 4 are moved in the direction indicated by the arrows. In this case, when the step motors 5a and 6a are started, they are gradually accelerated and are subsequently driven at a constant speed. When the step motors 5a and 6a are to be stopped, they are gradually decelerated from the constant speed. If the slit members 3 and 4 are moved in accordance with such changes in speed of the motors, irregularity occurs in a radiographic image. In order to prevent such inconvenience, a slit member moving unit 17 includes microswitches 15 and 16 for detecting constant speed positions, as shown in FIG. 4. The microswitch 15 is arranged at a position where it is turned off by the slit mounting base 13 when the base 13 is moved to a position where the base 13 reaches the constant speed from the start speed. In response to the OFF operation of the microswitch 15, the high voltage controller 2 applies a high voltage to the X-ray tube 1 to cause it to radiate X-rays. The microswitch 16 is arranged at a position where it is turned on by the slit mounting base 13 when the base 13 is moved in the direction indicated by the arrow, and the constant speed is changed to the stop speed (deceleration speed). In response to the ON operation of the microswitch 16, the high voltage controller 2 stops the supply of the high voltage to the X-ray tube 1.

In the above-described arrangement, when the high voltage controller 2 energizes the X-ray tube 1 in response to the OFF operation of the microswitch 15, X-rays radiated from the X-ray tube 1 are formed into a single X-ray fan beam by the linear slit 3b. The X-ray fan beam is radiated on the subject 8. The single X-ray fan beam which is transmitted through the subject 8 is further narrowed down by the linear slit 4b and is incident on a film cassette 9. At this time, the slit members 3 and 4 are respectively moved by the step motors 5a and 6a controlled by control signals from the controller 7a while the centers of the slits 3b and 4b are aligned with the focal point of the X-ray tube 1, as shown in FIG. 3. With this operation, the subject 8 is scanned by the X-rays, and a radiographic is formed on a film of the film cassette 9.

When the slit mounting base 13 is positioned under the microswitch 16, the microswitch 16 is turned on, and the high voltage controller 2 deenergizes the X-ray tube 1. As a result, X-ray radiation from the X-ray tube 1 is stopped. In this manner, the X-ray radiation timing is synchronized with the movement of the slit members 3 and 4. Therefore, if the film cassette 9 is replaced with an X-ray detector, a conventional radiographic apparatus and image processor can be directly used for the present invention, and can be simplified in arrangement. In addition, since the apparatus includes the two slit members 3 and 4, scattered X-rays can be effectively removed. Hence, an image faithfully reflecting the absorption coefficient of each human organ can be obtained, and detection ability of a morbid portion can be greatly improved.

Figure 5:
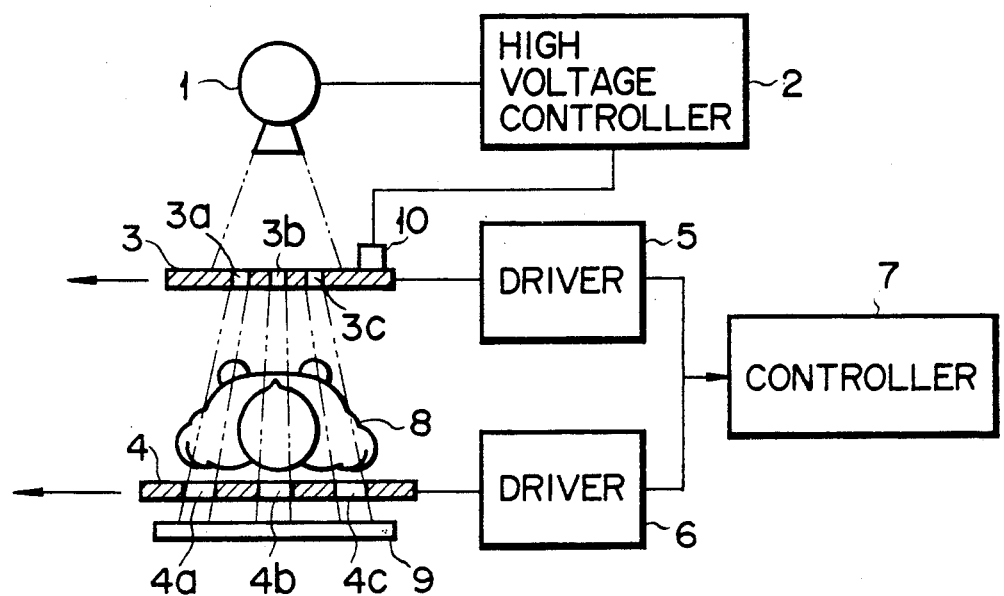
FIG. 5 is a schematic view showing an arrangement of a radiographic apparatus using multi-slit members according to another embodiment of the present invention.
Figure 6:
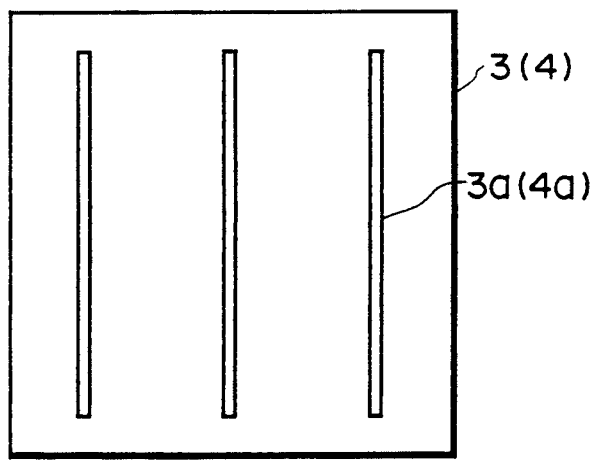
FIG. 6 is a plan view of one of the multi-slit members used in the apparatus in FIG. 5.

An embodiment using multi-slit members will be described below with reference to FIG. 5.

In this embodiment, slit members 3 and 4 each have three slits, i.e., slits 3a to 3c (4a to 4c), arranged at equal intervals. In this case, the opening centers of the slit pairs of the slit members 3 and 4, i.e., the slits 3a and 4a, the slits 3b and 4b, and the slits 3c and 4c are respectively aligned with the tube focal point of an X-ray tube 1. The width of each slit formed in the lower slit member 4 is set to be larger than that of each slit formed in the upper slit member 3. The width of each slit varies in accordance with the number of slits to be formed in a slit member. For example if 3, 6, or 12 slits are to be formed in the lower slit member, the width of each slit is set to be 4 mm, 2 mm, or 1 mm dependent upon the allowable load of the X-ray tube 1.

According to the embodiment using the above-described multi-slit members, X-rays radiated from the X-ray tube 1 are formed into three X-ray fan beams by the linear slits 3a to 3c and are radiated on the subject 8. The three X-ray fan beams which are transmitted through the subject 8 are narrowed down by the linear slits 4a, 4b, and 4c of the slit member 4 and are incident on the film cassette 9. The slit members 3 and 4 are moved relative to the subject 8 by drivers 5 and 6 controlled by control signals from a controller 7. With this operation, the subject 8 is scanned by the three X-ray fan beams narrowed down by the linear slits 3a to 3c.

If a slit member having three slits is used in the above-described manner, the moving distance of the slit member is reduced to ⅓ that of a slit member having one slit. This allows a shorter radiographing time, a smaller radiographing apparatus, a shorter radiographing time interval (continuous radiography) associated with the allowable load of the X-ray tube, and a longer service life of the X-ray tube bulb.

Another embodiment of the present invention will be described below with reference to FIG. 7A.

In this embodiment, edge angles $\theta 1$ and $\theta 2$ (see FIG. 8) of linear slits 3a and 4a are set to be equal to an angle $\theta$ defined by lines connecting slit members 3 and 4, a focal point 18, and an edge of a film cassette 9, i.e., the maximum X-ray radiation angle. In addition, the linear slit 3b of the slit member 3 has a width L1, and the linear slit 4b has a width L2. The slit width ratio L1/L2 of the linear slits 3a and 4a is set as follows:

$$L1/L2 = kd1/d2$$

where k is determined by the initial positioning precision of the focal point 18 and the linear slits 3a and 4a, the process precision of the linear slits 3a and 4a, and the synchronous driving precision of the slit members 3 and 4.

If the edge angles of the slits are set at a maximum angle of X-ray emission and the slit width ratio at a value of $kd1/d2$ ($k>1$), X-rays can always be shielded by edges 4f of the tube-side surface of an X-ray shielding plate 4d retardless of the positions of the linear slits 3a and 4a. This allows a uniform X-ray radiation amount throughout an irradiated region. Hence, a high-quality X-ray image can be obtained.

X-rays radiated from an X-ray tube are shielded by an X-ray shielding plate of the slit member 3, and is further shielded by the X-ray shielding plate 4d of the slit member 4. Therefore, the X-ray shielding plate 4d of the slit member 4 is formed to be relatively thin enough to remove scattered X-rays in an area outside a portion where the X-ray shielding portions of the X-ray shielding plates overlap each other, i.e., a range defined by alternate long and two short dashed lines in FIG. 7A. In other words, the X-ray shielding portion other than the X-ray shielding portion close to the slit 4a which directly receives X-rays passing through the slit 3a of the upper slit member 3 is formed to be relatively thin. This can reduce the slit member 4 in weight. In addition, the rigidity of the X-ray shielding plate 4d can be maintained by bonding a resin plate 4e to the X-ray shielding plate 4d.

In FIG. 7B, the lower slit member 4 has a slit 4a having a width larger than the size of the X-ray beam passing through the slit 3a of the upper slit member 3 and incident on the slit member 4, that is, the slit width ratio is set at $kd1/d2$ ($k<1$). Accordingly, the X-ray beam passing through the slit 3a completely passes through the slit 4a, that is, it is not shielded by the X-ray shielding plate 4d. As a result, the embodiment of FIG. 7B provides a contrast equal to that of FIG. 7A with the amount of X-rays to the subject being decreased in comparison with the case of FIG. 7A.

Still another embodiment of the present invention will be described below with reference to FIG. 9.

This embodiment includes an auxiliary shielding member 19. When the two slit members 3 and 4 are to be used as shown in FIG. 3, an X-ray radiation time interval must be accurately matched with a moving time of the slit members 3 and 4. In a currently available X-ray tube and high voltage controller, since repeatability of a radiation time interval cannot be accurately ensured, it is difficult to match these times. If an X-ray radiation time interval becomes longer than a preset value, X-rays are excessively radiated on a film cassette 9. If it is too short, a shortage of radiation dose is caused. As a result, linear stripes may be produced in an image at slit intervals.

Figure 9:
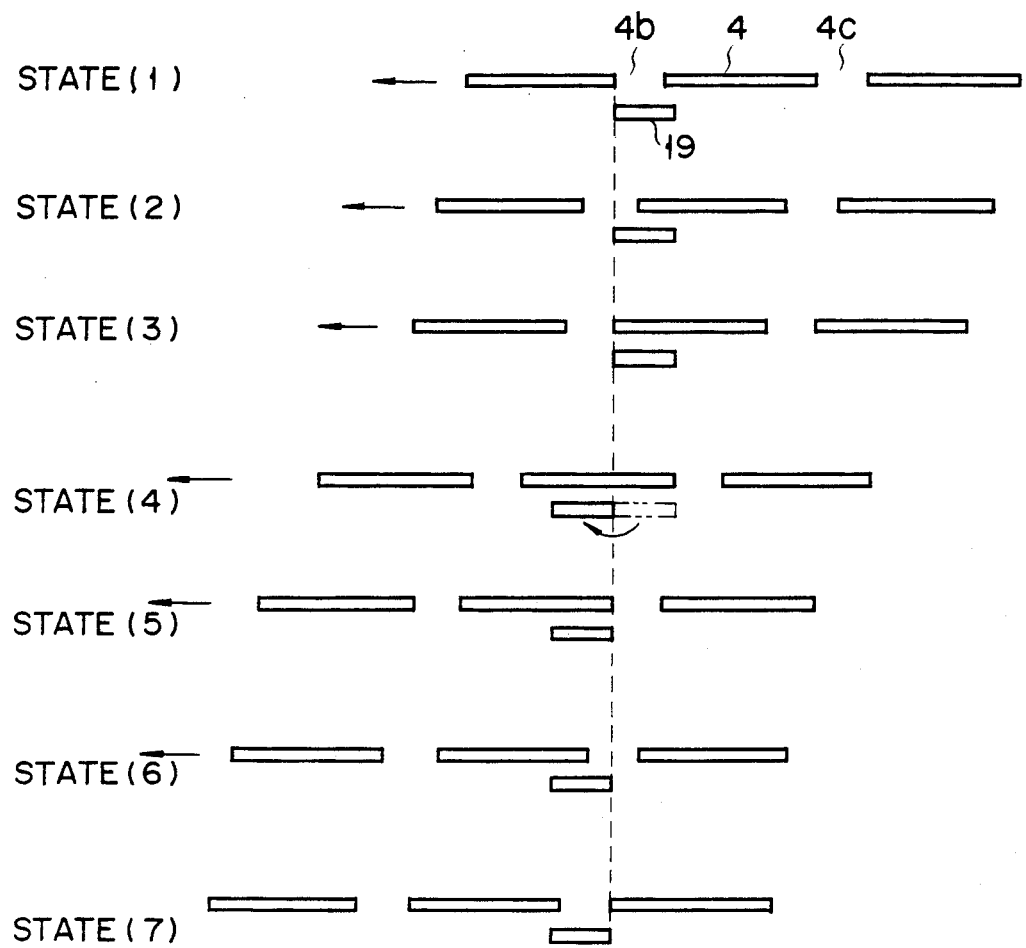
FIG. 9 is a view showing a positional relationship between a slit member and an auxiliary X-ray shielding member of a radiographic apparatus according to still another embodiment of the present invention.

This embodiment, therefore, comprises the auxiliary X-ray shielding member 19 below a slit member 4, as shown in FIG. 9. Referring to FIG. 9, a state (1) indicates the moment at which X-ray radiography is started. Radiation of X-rays is started from this state, and the slit member 4 begins to move at a constant speed v in a direction indicated by an arrow. The X-rays which are transmitted through a subject are incident on the film cassette 9 through a gap between a slit edge of the slit member 4 and an edge of the auxiliary X-ray shielding member 19. As indicated by states (2) and (3), the X-rays radiated toward the film cassette 9 pass through a slit 4b which is gradually opened as the slit member 4 is moved, thus slit-exposing the film cassette 9. When the auxiliary X-ray shielding member 19 is completely covered by an X-ray shielding plate of the slit member 4, the member 19 is rotated clockwise through 180°, as indicated by a state (4). Subsequently, as indicated by states (5) to (7), the X-rays which are transmitted through the subject pass through an X-ray path formed by a slit 4c and the auxiliary X-ray shielding plate 19, thus exposing the film cassette 9.

By using the auxiliary X-ray shielding member 19 in the above-described manner, boundaries of the slits 4b and 4c are accurately matched with each other, and an X-ray image having no stripes can be obtained. In addition, since X-ray radiation start and stop timings can be arbitrarily set within a time interval in which the slits (4b, 4c) are closed by the auxiliary X-ray shielding member 19, no high X-ray radiation precision is required, and X-ray radiation can be accurately controlled.

An apparatus for driving the auxiliary shielding member 19 will be described below with reference to FIG. 10.

Figure 10A:
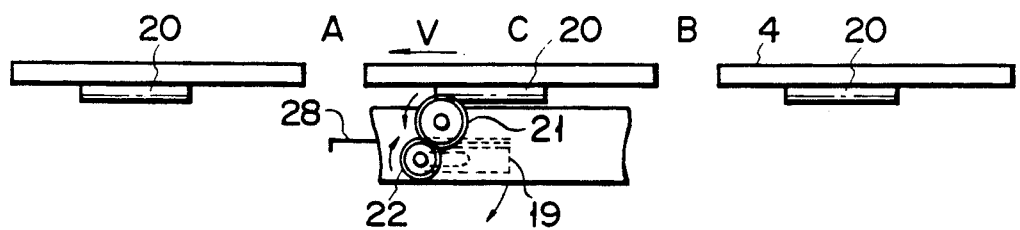
FIGS. 10A and 10B are side and plan views showing a driving unit for driving the auxiliary X-ray shielding member in FIG. 9.
Figure 10B:
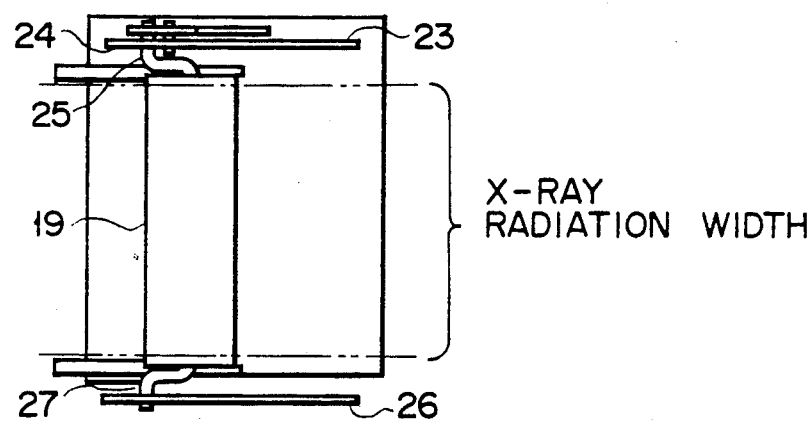

As shown in FIG. 10, a rack 20 is mounted on a lower portion of the slit member 4. The rack 20 is engaged with a gear 21, and rotates the gear 21 as the slit member 4 is moved at the constant speed v in a direction indicated by an arrow. The gear 21 and a gear 22 meshed therewith are mounted on a plate 23 through a bearing 24. The auxiliary shielding member 19 is held on the plate 23 and a plate 26 by arms 25 and 27.

In the above-described structure, when the gear 21 is rotated counterclockwise by the rack 20, the gear 22 is rotated clockwise. The auxiliary X-ray shielding member 19 is fixed to the gear 22 through the arm 25 and is rotated clockwise through 180° while is covered with a shielding portion of the slit member 4 in accordance with the mounting position and the number of teeth of the rack 20.

Figure 11:
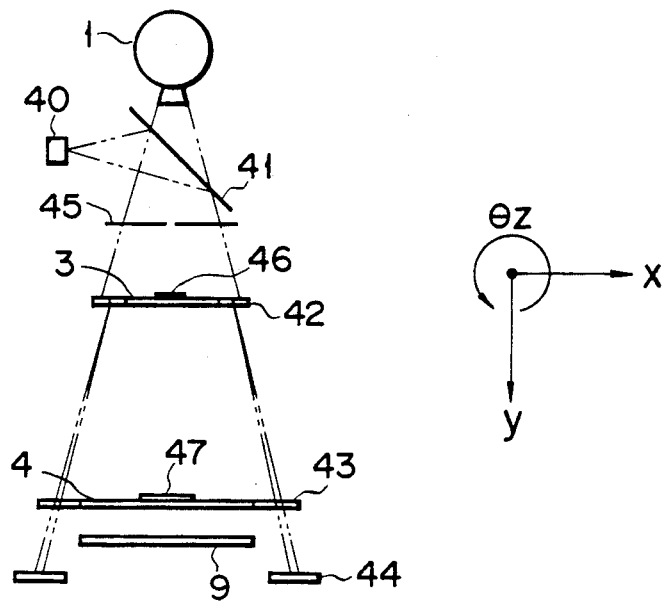
FIG. 11 is a schematic view showing an arrangement of a radiographic apparatus using a visible laser beam according to still another embodiment of the present invention.

Another embodiment of the present invention will be described below with reference to FIG. 11.

In this embodiment, a visible light semiconductor laser 40 is arranged at a position where its oscillating portion is symmetric with respect to a mirror 41. Oscillated light from the visible light semiconductor laser 40 is narrowed down by a detachable pinhole member 45, and is reflected by a mirror 46 bonded parallel to a slit member 3. When this reflected light is deviated from the center of the pinhole member 45, the angle (perpendicularity) of the slit member with respect to the optical axis is detected from this deviation. This angle (perpendicularity) is adjusted by a rotating mechanism attached to the slit member 3. The angle (perpendicularity) of a slit member 4 is also detected by a mirror and is adjusted in the same manner as described above. With this operation, the slit members 3 and 4 are set to be parallel to each other.

Subsequently, the pinhole member 45 is detached. The oscillated light from the visible light semiconductor laser 40 passes through positioning slits 42 and 43 respectively formed in the slit members 3 and 4 and reaches a projection screen 44 with graduations. A relative positional relationship between the X-ray tube 1 and the slits of the slit member 3 and 4 can be determined from a photopattern projected on the projection screen 44.

A method of detecting a positional error by using a photopattern will be described below with reference to FIGS. 12 and 13A to 13F.

Figure 13C:
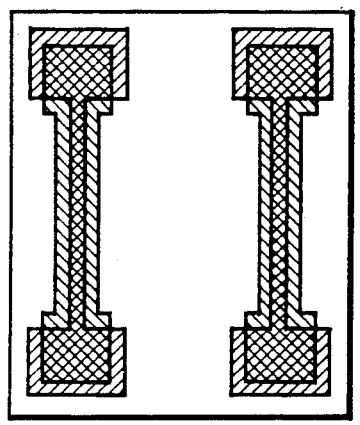
Figure 13D:
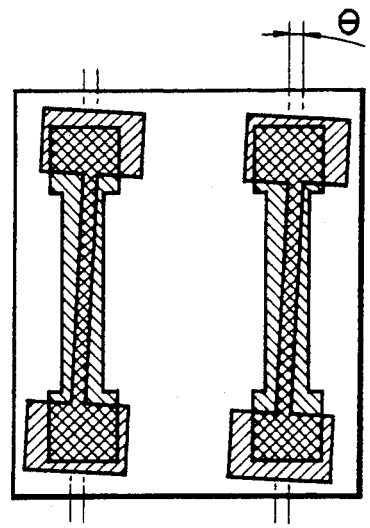
Figure 13E:
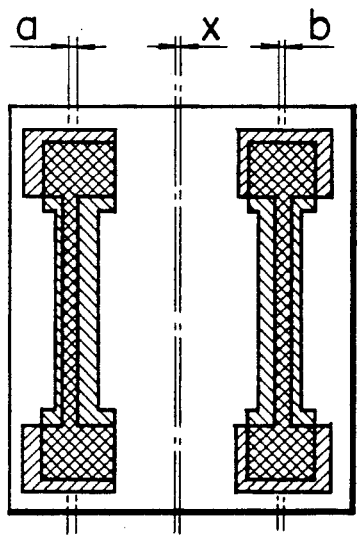
Figure 13F:
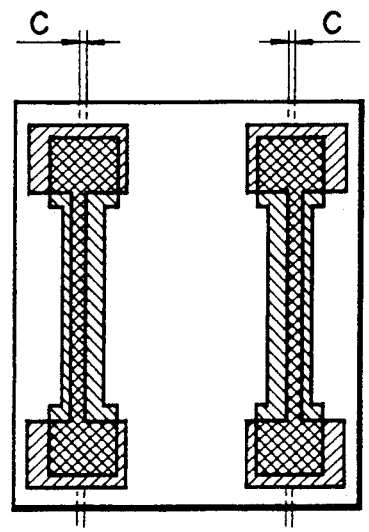

FIGS. 13A and 13B respectively show the shapes of the positioning slits 42 and 43. FIG. 13C shows a photopattern obtained when no positional error is caused between the X-ray tube 1 and the slit members 3 and 4. FIGS. 13D, 13E, and 13F respectively show photopatterns obtained when positional errors in the θ, X, and Y directions are present. According to this photopattern detecting method, a photopattern is adjusted by a two-dimensional (X, Y) traverse mechanism rotating (θ) mechanism arranged in one of the slit members 3 and 4, as shown in FIG. 13C, and a positional error of each slit member can be easily detected.

According to the present invention, since a two-dimensional recording medium, i.e., a film cassette, is used as an X-ray detector, a conventional X-ray diagnosis apparatus and image processor can be used without modifications, and the arrangement of the apparatus can be simplified. Since the apparatus of the present invention includes the two slit members having linear slits, scattered X-rays can be effectively removed, and an image faithfully reflecting the absorption coefficient of each human organ can be obtained, thereby greatly improving detection ability of a morbid portion.

By using the multi-slit members, the moving distance of each slit member can be reduced, thus allowing a smaller photographing unit, a shorter radiographing time, a shorter radiographing time interval (continuous photography) associated with the allowable load of an X-ray source, and a longer service life of the X-ray source.

In addition, by matching the angle of the slit edges for shielding X-rays with the X-ray radiation angle to obtain a desirable slit width ratio, a substantially uniform X-ray radiation amount can be realized throughout an entire X-ray detecting surface without the necessity of accurately positioning both slits, whereby an image having no errors can be obtained.

Furthermore, since the auxiliary X-ray shielding member is arranged for the slit member, no high X-ray radiation time interval precision is required, and an X-ray radiation amount can be accurately controlled.

Moreover, by using a position detecting light source, positional errors between the X-ray source and the two slit members can be quickly and accurately detected, and can be corrected.

Additional advantages and modifications will readily occur to those skilled in the art. Therefore, the invention in its broader aspects is not limited to the specific details, and representative devices, shown and described. Accordingly, various modifications may be made without departing from the spirit or scope of the general inventive concept as defined by the appended claims and their equivalents.

What is claimed is:

1. A radiographic apparatus comprising:
X-ray source means, having an X-ray tube focal point, for radiating X-rays from the focal point;
two slit members sequentially arranged to oppose said X-ray source means, a subject being arranged between said slit members, and each of said slit members having at least one linear slit for narrowing the X-rays radiated from said X-ray source means to obtain a slit-like X-ray beam;
driving means for moving said slit members and the object relative to each other in such a manner that the X-ray tube focal point and the slits of said slit members are always aligned with each other; and
recording means for two-dimensionally recording a slit-like X-ray beam obtained by causing the X-rays radiated from the said X-ray source means to pass through the subject and the linear slits of said slit members;
said slit members including a first slit member directly opposing said X-ray source means, and a second slit member, arranged below said first slit member, for narrowing a slit-like X-ray beam which passes through at least one slit of said first slit member and the subject, said second slit member having a first X-ray shielding portion close to the slit and directly receiving the X-rays passing through the slit of said first slit member, and a second X-ray shielding portion which is formed to be thinner than said first X-ray shielding portion.

2. An apparatus according to claim 1, wherein said driving means comprises slit moving means, coupled to said slit members, for horizontally moving said slit members, and a control means for controlling said slit moving means so as to keep the X-ray tube focal point and the slits of said slit members aligned with each other.

3. An apparatus according to claim 2, wherein said slit moving means comprises two screw shafts threadably engaged with said slit members, respectively, and two motors, respectively coupled to said screw shafts, for rotating said screw shafts.

4. An apparatus according to claim 1, wherein said slit moving means comprises detecting means for detecting a position where said slit members are moved at a constant speed, and outputting a detection signal, and said X-ray source means generates X-rays while said slit members are moved at a constant speed, in response to the detection signal.

5. An apparatus according to claim 4, wherein said detecting means comprises first detecting means arranged at a position where a start speed of said slit members reaches a predetermined speed, and second detecting means arranged at a position where the predetermined speed is shifted to a stop speed.

6. An apparatus according to claim 1, wherein each of said slit having members includes a slit having an edge angle corresponding to a maximum radiation angle with respect to a focal point of said X-ray source means.

7. A radiographic apparatus comprising:

X-ray source means, having an X-ray tube focal point, for radiating X-rays from the focal point;

two multi-slit members sequentially arranged to oppose said X-ray source means, a subject being arranged between said multi-slit members, and each of said slit members having an X-ray shielding plate, and a plurality of linear slits, formed in said shielding plate at equal intervals, for narrowing the X-rays radiated from said X-ray source means to obtain a plurality of slit-like X-ray beams;

driving means for moving said multi-slit members and the subject relative to each other in such a manner that the X-ray tube focal point and the slits of said multi-slit members are always aligned with each other; and recording means for two-dimensionally recording the slit-like X-ray beams obtained by causing X-rays radiated from said X-ray source means to pass through the subject and the linear slits of said multi-slit members;

said multi-slit members including a first slit member directly opposing said X-ray source means and a second slit member, arranged below said first slit member, for narrowing the slit-like X-ray beams which pass through the slits of said first slit member and the subject, said second slit member having a first X-ray shielding portion close to the slits and directly receiving X-rays passing through the slit of said first slit member, and a second X-ray shielding portion which is formed to be thinner than said first X-ray shielding portion.

8. An apparatus according to claim 7, wherein each of said multi-slit members includes a slit having an edge angle corresponding to a maximum radiation angle with respect to a focal point of said X-ray source means.

9. An apparatus according to claim 8, wherein each of said slits of each of said multi-slit members includes a linear slit having a predetermined edge angle corresponding to a maximum X-ray radiation angle.

10. A radiographic apparatus comprising:

X-ray source means, having an X-ray tube focal point, for radiating X-rays from the focal point;

two multi-slit members sequentially arranged to oppose said X-ray source means, a subject being arranged between said multi-slit members, and each of said slit members having an X-ray shielding plate, and a plurality of linear slits, formed in said shielding plate at equal intervals, for narrowing the X-rays radiated from said X-ray source means to obtain a plurality of slit-like X-ray beams;

driving means for moving said multi-slit members and the subject relative to each other in such a manner that the X-ray tube focal point and the slits of said multi-slit members are always aligned with each other;

recording means for two-dimensionally recording the slit-like X-ray beams obtained by causing X-rays radiated from said X-ray source means to pass through the subject and the linear slits of said multi-slit members; and correcting means for correcting positional errors between the slits of said slit members and the X-ray tube focal point of said X-ray source means.

11. An apparatus according to claim 10, wherein said correcting means comprises:

a light source;

first and second mirrors respectively disposed on said two multi-slit members; and a pin hole member disposed between said light source and said two multi-slit members;

wherein respective positions of said two multi-slit members are determined by deviation of light from a center of the pin hole member reflected from said first and second mirrors.

12. An apparatus according to claim 7, wherein said driving means comprises slit moving means, coupled to said multi-slit members, for horizontally moving said multi-slit members, and control means for controlling said slit moving means so as to keep the X-ray tube focal point and the slits of said multi-slit members aligned with each other.

13. An apparatus according to claim 12, wherein said slit moving means comprises two screw shafts threadably engaged with said multi-slit members, respectively, and two motors, respectively coupled to said screw shafts, for rotating said screw shafts.

14. An apparatus according to claim 7, wherein said slit moving means comprises detecting means for detecting a position where said multi-slit members are moved at a constant speed, and outputting a detection signal, and said X-ray source means generates X-rays while said multi-slit members are moved at the constant speed, in response to the detection signal.

15. An apparatus according to claim 14, wherein said detecting means comprises first detecting means arranged at a position where a start speed of said multi-slit members reaches a predetermined speed, and second detecting means arranged at a position where the predetermined speed is shifted to a stop speed.

16. A radiographic apparatus comprising:

X-ray source means, having an X-ray tube focal point, for radiating X-rays from the focal point;

two multi-slit members sequentially arranged to oppose said X-ray source means, a subject being arranged between said multi-slit members, and each of said slit members having an X-ray shielding plate, and a plurality of linear slits, formed in said shielding plate at equal intervals, for narrowing the X-rays radiated from said X-ray source means to obtain a plurality of slit-like X-ray beams;

driving means for moving said multi-slit members and the subject relative to each other in such a manner that the X-ray tube focal point and the slits of said multi-slit members are always aligned with each other;

recording means for two-dimensionally recording the slit-like X-ray beams obtained by causing X-rays radiated from said X-ray source means to pass through the subject and the linear slits of said multi-slit members; and an auxiliary X-ray shielding member, arranged near one of said slit members, for matching an X-ray radiation time interval with a moving time of said slit members, said auxiliary X-ray shielding member being provided so that the X-rays transmitted through the subject are incident on the recording means through a gap between a slit edge of said one of said slit members and an edge of said auxiliary X-ray shielding member.

17. An apparatus according to claim 10, further comprising means for rotating said auxiliary X-ray shielding member through 180° when said auxiliary X-ray shielding member is completely covered by X-ray shielding plate.

18. An apparatus according to claim 11, comprising: said auxiliary X-ray shielding member being disposed to completely block X-rays emitted through said one of said slit members at an onset of said X-ray radiation time interval, said one of said slit members being moved relative to said auxiliary shielding member thereby gradually opening said gap.

* * * * *